(12) United States Patent
Garguilo et al.

(10) Patent No.: US 6,344,145 B1
(45) Date of Patent: Feb. 5, 2002

(54) DEVICE TO IMPROVE DETECTION IN ELECTRO-CHROMATOGRAPHY

(75) Inventors: Michael G. Garguilo; Phillip H. Paul, both of Livermore; David J. Rakestraw, Fremont, all of CA (US)

(73) Assignee: Sandia Corporation, Livermore, CA (US)

( * ) Notice: Subject to any disclaimer, the term of this patent is extended or adjusted under 35 U.S.C. 154(b) by 0 days.

(21) Appl. No.: 09/546,290

(22) Filed: Apr. 10, 2000

Related U.S. Application Data

(62) Division of application No. 09/182,124, filed on Oct. 29, 1998, now Pat. No. 6,068,767.

(51) Int. Cl.⁷ .............................................. B01D 15/08
(52) U.S. Cl. ................... 210/635; 210/656; 210/198.2; 204/455; 204/605
(58) Field of Search ................. 210/635, 656, 210/198.2; 204/455, 604, 605, 453

(56) References Cited

U.S. PATENT DOCUMENTS

| | | | |
|---|---|---|---|
| 3,782,078 A | * 1/1974 | Jerpe | 210/198.2 |
| 4,293,415 A | * 10/1981 | Bente | 210/198.2 |
| 4,793,920 A | * 12/1988 | Cortes | 210/198.2 |
| 5,061,361 A | * 10/1991 | Gordon | 210/198.2 |
| 5,246,577 A | * 9/1993 | Fuchs | 210/198.2 |
| 5,531,959 A | * 7/1996 | Johnson | 210/198.2 |
| 5,540,464 A | * 7/1996 | Picha | 210/198.2 |
| 5,611,904 A | * 3/1997 | Cole | 210/198.2 |
| 5,679,255 A | * 10/1997 | Cortes | 210/198.2 |
| 5,714,074 A | * 2/1998 | Karlsson | 210/198.2 |
| 5,759,405 A | * 6/1998 | Anderson | 210/198.2 |
| 5,858,241 A | * 1/1999 | Dittmann | 210/198.2 |
| 5,908,552 A | * 6/1999 | Dittmann | 210/198.2 |

* cited by examiner

*Primary Examiner*—Ernest G. Therkorn
(74) *Attorney, Agent, or Firm*—Donald A. Nissen

(57) ABSTRACT

Apparatus and method for improving the resolution of non-pressure driven capillary chromatographic systems, and particularly for capillary electrochromatography (CEC) systems. By reducing the cross-sectional area of a packed capillary column by means of a second open capillary contiguous with the outlet end of a packed capillary column, where the packed capillary column has a cross sectional area of between about 2 and 5 times that of the open capillary column, the phenomenon of band broadening in the transition region between the open capillary and the packed capillary column, where the individual components of the mixture are analyzed, can be eliminated, thereby providing for a significant improvement in resolution and more accurate detection and analysis.

3 Claims, 2 Drawing Sheets

DEVICE TO IMPROVE DETECTION IN ELECTRO-CHROMATOGRAPHY

CROSS-REFERENCE TO RELATED APPLICATIONS

This application is a Division of prior Application Ser. No. 09/182,124, filed Oct. 29, 1998, now U.S. Pat. No. 6,068,767.

STATEMENT OF GOVERNMENT INTEREST

This invention was made with Government support under contract no. DE-AC04-94AL85000 awarded by the U. S. Department of Energy to Sandia Corporation. The Government has certain rights in the invention.

BACKGROUND OF THE INVENTION

The present invention is directed to a device for improving the ability to detect components of a mixture in capillary electrochromatographic separations by eliminating band broadening at the transition region between a packed column and an analysis region.

In liquid chromatography, chemical separations can be performed by flowing a fluid (the mobile phase) past an immobilized material (the stationary phase) inside a liquid chromatography (LC) column. This technique is used for chemical analysis by injecting a sample consisting of multiple components into one end of the LC column, causing the individual components comprising the sample to be separated into distinct and discrete bands as the sample flows through the LC column, and detecting those bands near the exit end (typically within 2–3 channels diameters of the end of the stationary phase) of the LC column. Separation is governed by the dynamic partitioning of the analyte between the mobile phase and the stationary phase. Control of the separation may be achieved by adjusting the composition of the mobile phase or the stationary phase or both to influence analyte partitioning. In some chromatographic methods, such as capillary zone electrophoresis (CZE) and capillary electrochromatography (CEC) an electric field is applied to the chromatographic column to enhance separation.

In CEC, a capillary column is packed with a stationary phase material similar to that used in micro high pressure liquid chromatography (HPLC). The mobile phase, however, is caused to flow through the capillary column by an applied electric field that creates an electro-osmotic flow, similar to that in CZE, rather than using high pressure mechanical pumps, as in HPLC. The CEC approach can thus achieve the high efficiency of CZE. In addition, as in the case with micro-HPLC, CEC may be used to analyze neutral compounds that are not separable by CZE. The miniaturization of the separation column by using a capillary column in CEC offers several advantages, including improved efficiency, mass detection sensitivity, low solvent consumption, small sample quantity, and easier coupling to detector such as mass spectrometers and flame-based detectors.

A growing interest has developed in portable devices that will permit the rapid analysis of minute quantities of various chemical agents, and mixtures thereof, in a non-laboratory setting (i.e., "in the field"). Chromatography, and particularly CEC, offers a means for separating the various components of a mixture for subsequent detection and analysis "in the field" and numerous microcolumn chromatographic separations schemes have been developed that are capable of both rapid and efficient separation of complex mixtures.

However, these two goals of fast and efficient analysis of the components of a mixture tend to be mutually exclusive. Reduction in chromatographic analysis time is usually achieved by forcing the sample through the chromatographic column rapidly. This approach sacrifices much of the separation efficiency of the chromatographic column, resulting in a phenomenon known as band broadening which degrades the resolution of the separation, i.e., the ability to separate out compounds having similar chemical structures will be lost. A second approach can be to shorten the column length. However, here also there will be a decrease in column efficiency which can be partially offset by reducing the chromatographic dimensions, such as by reducing the particle size of the stationary phase. This miniaturization introduces a new set of problems and, even here, it has been observed that band broadening can take place.

As will be shown in greater detail below, it is possible to eliminate, or significantly reduce, broadening of eluted bands by modifications to the column packing and/or the ionic strength or pH of the solution. However, this solution can be quite complex, requiring significant trial and error. A simpler solution, contraction of the column diameter in the region immediately downstream the stationary phase, has been shown to be equally effective in eliminating broadening of bands being eluted from the stationary phase of the column.

SUMMARY OF THE INVENTION

By eliminating the phenomenon of band broadening in capillary electrochromatography (CEC) systems the present invention provides for a significant improvement in the resolution and thus, more accurate detection and analysis of the bands which comprise the components of the mixture being analyzed. As disclosed herein, the phenomenon of particular concern, band broadening, takes place in the transition region where bands corresponding to the components of a mixture being analyzed are eluted from the stationary phase and into an analysis section, a region typically within 2–3 column diameters of the stationary phase. A novel device for eliminating the phenomenon of band broadening comprising contraction of the capillary column diameter in the region immediately downstream the stationary phase is described. Contraction of the capillary column diameter is accomplished by joining an open capillary contiguous with the outlet end of a capillary column packed with a stationary phase, wherein the open column has a cross-sectional area of from about 0.2 to 0.5 times that of the packed capillary column.

It is, therefore an object of the present invention to provide a method for improving the resolution of non-pressure driven capillary chromatographic systems, and particularly for capillary electrochromatography (CEC) systems columns by minimizing or eliminating conditions which lead to spreading or broadening of eluted bands at the point of analysis.

A further object of this invention is to improve the sensitivity of CEC separations.

DETAILED DESCRIPTION OF THE INVENTION

In capillary electrochromatography (CEC) a liquid mixture, which is to be separated into its components and the components identified and quantified, is introduced as a "plug" into a separation column and allowed to traverse the column under the influence of an applied electric field. The separation column generally comprises a fused silica capillary tube, that can or cannot be circular in cross-section. A portion of the capillary column is packed with a stationary solid phase (that can be fused silica particles about 1 to 3 $\mu$m in diameter) held in place with porous frits which are typically sintered silica particles disposed at the upstream (inlet) and downstream (outlet) 120 ends of the column. Under the combined effects of gravitational flow, ionic drift, induced by the applied electric field, and the retarding effect of the stationary phase, the mixture is separated into bands. If the column has been designed correctly and the proper operating conditions employed (which can include ionic strength and pH of the solution), each band will contain a separate component of the mixture and each band will be distinct and discrete, separated from the other bands in space and time, and each band will be eluted from the packed column in serial fashion. To avoid disturbing the stationary phase of the packed capillary column, detection and analysis of the various components of the mixture typically takes place in an unpacked, or open, portion of the capillary column 110 adjacent the downstream frit 120 where the bands corresponding to the individual components of the mixture emerge from the packed capillary column.

A common problem in micro-capillary chromatographic separations, in general, and CEC, in particular, is the phenomenon of band broadening. Rather than being distinctly separated in space and time, the bands corresponding to the individual components of a mixture are found to broaden and even coalesce, to a greater or lesser degree, into one another as they emerge from the packed column. As a result, the ability to analyze accurately the various components of a mixture as they elute from the packed column is degraded. Up to the present time, the reason for band broadening has not been understood. However, the inventors have discovered a mechanism for the phenomenon and the invention disclosed herein arises therefrom.

Figure 1A:
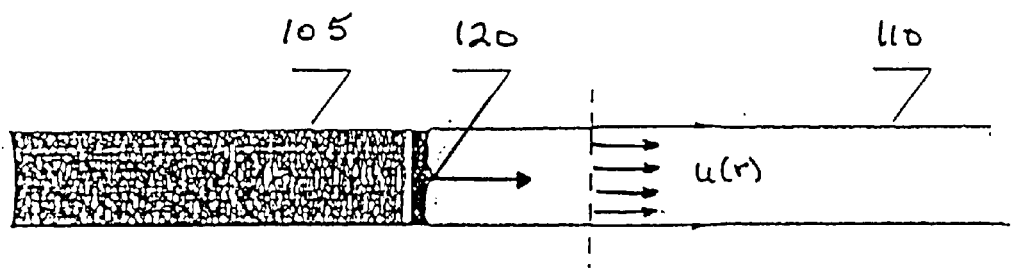
FIGS. 1a–1c illustrate the concept of the present invention.
Figure 1B:
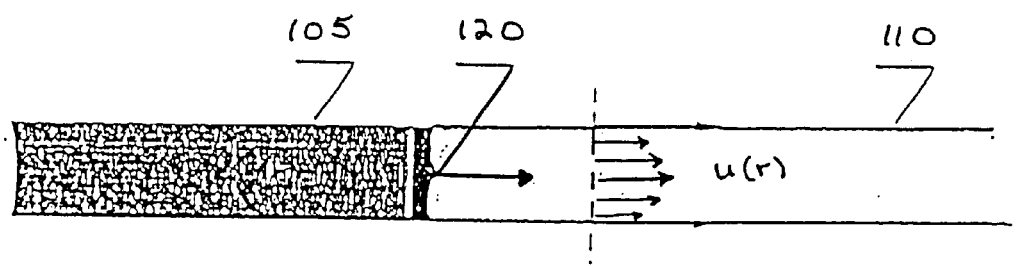
Figure 1C:
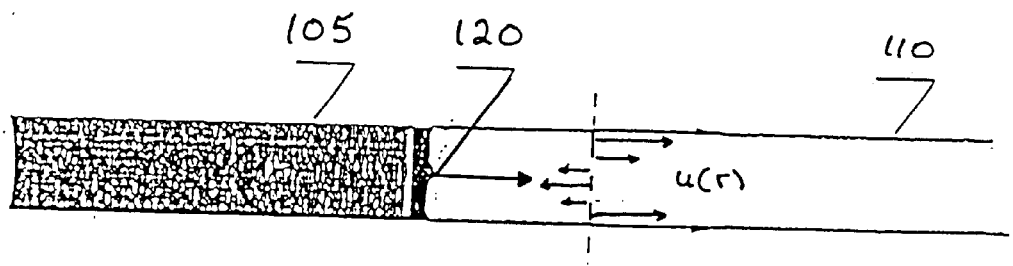

FIGS. 1a–1c illustrate the fundamental concepts embodied in the discussion below.

Consider a capillary or microchannel; the upstream portion 105 of which contains a porous material used to induce a separation and the downstream portion 110 of which is open. Detection is arranged to take place just downstream of the interface between these two sections. The volumetric flow rate in the open section is given by (here relationships are written for a capillary of radius R, these may be easily generalized to a microchannel of arbitrary cross section)

$$Q_o = 2\pi \int_0^{R_o} u(r) r\, dr = A_o u_{Eo} \frac{1}{R_o^2} \int_0^{R_o} \frac{u(r)}{u_{Eo}} d r^2 \quad (1)$$

Here u is the local fluid velocity, $R_o$ is the radius and $A_o$ the cross sectional area of the open section, and $U_{Eo}$ is the electroosmotic velocity. The volumetric flow rate in the packed section reduces to $$Q_P = A_P u_{Ep} \frac{\varphi}{\gamma^2} \quad (2)$$

Here $A_p$ is the total cross sectional area of the packed section, $\psi$ is the porosity and $\gamma$ the tortuosity of the packing, and $u_{Ep}$ the electroosmotic velocity in the packing. The electroosmotic velocities may be written as $$u_x = \frac{-\varepsilon}{\eta} \zeta_x E = \frac{-\varepsilon}{\eta} \zeta_x \frac{i}{\sigma_x A_x} \quad (3)$$

where the subscript x refers to either open or packed (o or p, respectively). Here $\epsilon$ and $\eta$ are the fluid permativity and viscosity, $\zeta$ the zeta potential, $\sigma$ the electrical conductivity and i the current. Given conservation of the current, equating the volume flow rates yields $$\frac{1}{R_o^2} \int_0^{R_o} \frac{u(r)}{u_{Eo}} d r^2 = \frac{\sigma_o}{\sigma_p} \frac{\zeta_p}{\zeta_o} \frac{\varphi}{\gamma^2} \equiv \lambda \quad (4)$$

Far downstream of the interface between the two sections, the velocity will have established a steady profile which must in general be parabolic with centerline velocity $u_{cl}$ and have a value of $$\frac{u_{cl}}{u_{Eo}} = 2\lambda - 1 \quad (5)$$

Alternatively, it can be shown that the quantity $$\lambda = \frac{\sigma_0}{\sigma_p} \frac{\zeta_{p,\mathit{eff}}}{\zeta_0} \frac{\varphi}{\gamma^2} \quad (6)$$

may be further simplified by observing that the effective conductivity of the packed section is in direct proportion to the bulk conductivity (i.e. $\sigma_p = F\sigma_o$, where F is by definition less than unity and typically of order 0.2), hence $$\lambda = \frac{1}{F} \frac{\zeta_p}{\zeta_o} \frac{\varphi}{\gamma^2} (1 - \xi) \quad (7)$$

where $\xi$ accounts for double layer overlap and is generally $0 \leq \xi \leq 1$.

The quantity $\lambda$ is a property of the system dependent on the internal structure of the packing (through F, $\psi$ and $\gamma$) and on the surface interfacial electrochemistry (through the zeta potentials) and is totally independent of the system geometry or flow rate or on the bulk conductivity of the fluid.

For $\lambda=1$ (FIG. 1a) the velocity profile is flat over the cross section of the column, which is the desired or ideal condition. For $\lambda>1$ (FIG. 1b) the velocity profile is forward parabolic (i.e. the velocity on centerline is greater than that at the walls). For $\lambda<1$ (FIG. 1c) the velocity profile is backwards parabolic (i.e. the velocity on centerline is less than that at the walls). For $\lambda=1/2$ flow is stopped on the centerline (i.e. $u_{cl}=0$). For $\lambda<1/2$ there is a reverse flow on centerline (i.e. $u_{cl}<0$). This reverse flow causes excessive stirring and broadening of the eluted band of material from the moment the band elutes from the stationary phase. Operation in this regime is unacceptable and it is necessary to increase the value of $\lambda$ by either altering the nature of the packing material and/or increasing the ratio of the zeta potential (cf. eqn. 4) to achieve a condition whereby $\lambda>1/2$.

For typical conditions: a packing of 1.5 $\mu$m diameter beads; 1 mM salts added to support the electrolyte; a porosity of 1/3 and $\gamma^2$ 2; $\sigma_o/\sigma_p \approx 4.5$, we then have $\lambda=0.75$ $\zeta_p/\zeta_o$ or for equal zeta potentials $\lambda=0.75$ thence $u_{cl}=0.5\ u_{Eo}$ there is thus a velocity deficit on the centerline.

We make several observations: 1) this result does not depend on the cross sectional area or the length of either the open or the packed sections of the capillary; 2) even for equal zeta potentials, the effective value of $\zeta_p$ will be reduced by double layer overlap, which leads to a value of $\lambda<1$ and to a further departure from ideal conditions; 3) alterations which increase the thickness of the double layer, by decreasing the concentration of the salts in the electrolyte or increasing $\zeta_p$, will increase the effect of double layer excess conduction hence increase the value of $\sigma_p$ with respect to $\sigma_o$ and thus worsen the situation, reducing $\zeta_o$ with respect to $\zeta_p$ can correct the problem. However, packing a capillary with a material of higher zeta potential leads to dispersion during the separation, thus this tactic will only work if the body of the packed section has a zeta potential similar to that of the packing and the body of the open section has a modified zeta potential selected to yield a value of $\lambda=1$. Further, this tactic may only be possible under a limited range of operating conditions (e.g. limited range of electrolyte composition or pH); 4) any useful system must have a value of $\lambda>1/2$ otherwise the resulting flow reversal will have the effect of efficiently stirring the fluid, irreversibly degrading the concentration profile of the eluted plug.

For most micro-capillary systems the value of the ratio $\zeta_p/\zeta_o$ is $\leq 1$ and, referring now to equation (7), it can be readily seen that $\lambda<1$, resulting in a fluid velocity profile similar to that illustrated in FIG. 1b. However, in order to analyze accurately the bands of material being eluted from the packed capillary it is necessary that the concentration profile, C(r,t) of the eluted material in space and time, have a reasonably flat profile through the detection region (the detection region being the first few, typically 2–3, capillary diameters immediately downstream of the interface). This can be accomplished by reducing the cross-sectional area of the capillary just downstream of the transition between the packed and open portions of the capillary. The reduction in cross-sectional area does not in fact correct the velocity profile, which, for reasons set forth above, will become parabolic further downstream, unless $\lambda=1$. Rather the reduction of the cross-sectional area of the capillary has the effect of delaying the fluid at the walls with respect to the fluid in the center of the channel and thus temporally counteracting the effect of the parabolic flow; a particle traveling along the wall will follow a longer path than the one on centerline. These effects combined can yield a reasonably flat eluted band profile for about 2 to 5 channel diameters downstream, sufficient to avoid major band broadening during detection.

The inventors have shown that without a reduction in capillary cross-sectional area just downstream of the transition region, and with $\lambda=0.75$, the profile of the eluted band of material is seriously broadened (by a factor of about 5 to 10 times) whereas with an immediate cross-sectional area reduction by a factor of about 2, broadening of the profile of the eluted band of material is almost completely avoided, as determined by flow imaging tests. For $\lambda=0.55$, modeling suggest that the area reduction needs to be about a factor of 4 to 5 to avoid degradation of the eluted band profile. That is, it is preferred that the ratio $A_p/A_o$, the ratio of the cross-sectional area of the packed section of the column to that of the open section, be from about 2 to 5. Obviously, at the ideal condition of $\lambda=1$ the ratio $A_p/A_o$ can be 1. It may be thought that the transition between the two capillaries be smooth, but this is not the case. In our experiments we find that there is no observable trapping of eluted material in the corners of the 'step' between the two areas. This is an expected characteristic of electroosmotic flow.

It should be noted that while the preceding discussion, illustrating the concept of the present invention, has been for a capillary column which is circular in cross-section, the same analysis applies to capillary columns or microchannels of any cross sectional shape. A microchannel is defined as a fluid passageway that can be etched or machined into a substrate, whose cross sectional area can be circular or noncircular, and has dimensions in the range of tens to hundreds of microns. Moreover, throughout the written description of the invention the terms capillary and microchannel are used synonymously and interchangeably.

Figure 2:
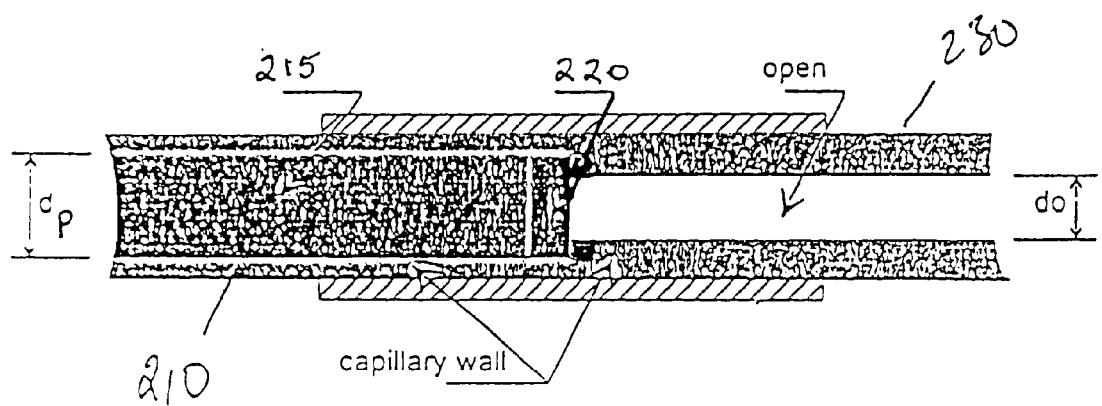
FIG. 2 is a diagrammatic view of one embodiment of the invention.

FIG. 2 is a diagrammatic view of one aspect of the present invention. A capillary tube 210 is provided with an upstream, or inlet, frit (not shown) and Hi a downstream, or outlet, frit 220, which define a volume within the capillary tube. The volume is packed with a particulate stationary phase 215. A second open capillary 230 is joined to packed capillary 210 adjacent downstream frit 220. The cross sectional area of second open capillary tube 230 can be from between about 0.2 and 0.5 times that of first packed capillary tube 210. Joining of the first and second capillaries can be by any method that will maintain the relative positions of the two capillaries such as sealing, gluing, or heat shrinkable Teflon tubing. It is preferred that the end of second capillary 230 be contiguous with downstream frit 220 of first capillary 215 in order that band broadening be negligible.

In a second aspect of the invention, microchannels are employed to effect the desired chromatographic separations. Here, a first microchannel, containing a stationary phase, is etched or machined into a substrate. A second microchannel, contiguous to the first microchannel and having a reduced cross-sectional area that can be from 0.2 to 0.5 times that of the first microchannel, is fabricated immediately downstream from the first microchannel.

It will be understood that the above described methods and arrangement of apparatus are merely illustrative of applications of the principles of this invention. Many other embodiments and modifications may be made without departing from the spirit and scope of the invention as defined in the claims.

We claim:

1. A method for improving the resolution of capillary systems, comprising:
   a) providing a capillary containing a stationary phase, the capillary having an inlet end and an outlet end; and
   b) providing a second capillary whose inlet end is contiguous with the stationary phase of the first capillary, wherein the second capillary is an open capillary and the ratio of the cross sectional areas of the packed and open capillaries, $A_p/A_o$, is between about 2 and 5.

2. The method of claim 1, wherein the first and second capillaries have a circular cross section.

3. The method of claim 1, wherein the first and second capillaries are microchannels.

* * * * *